Figure 1:
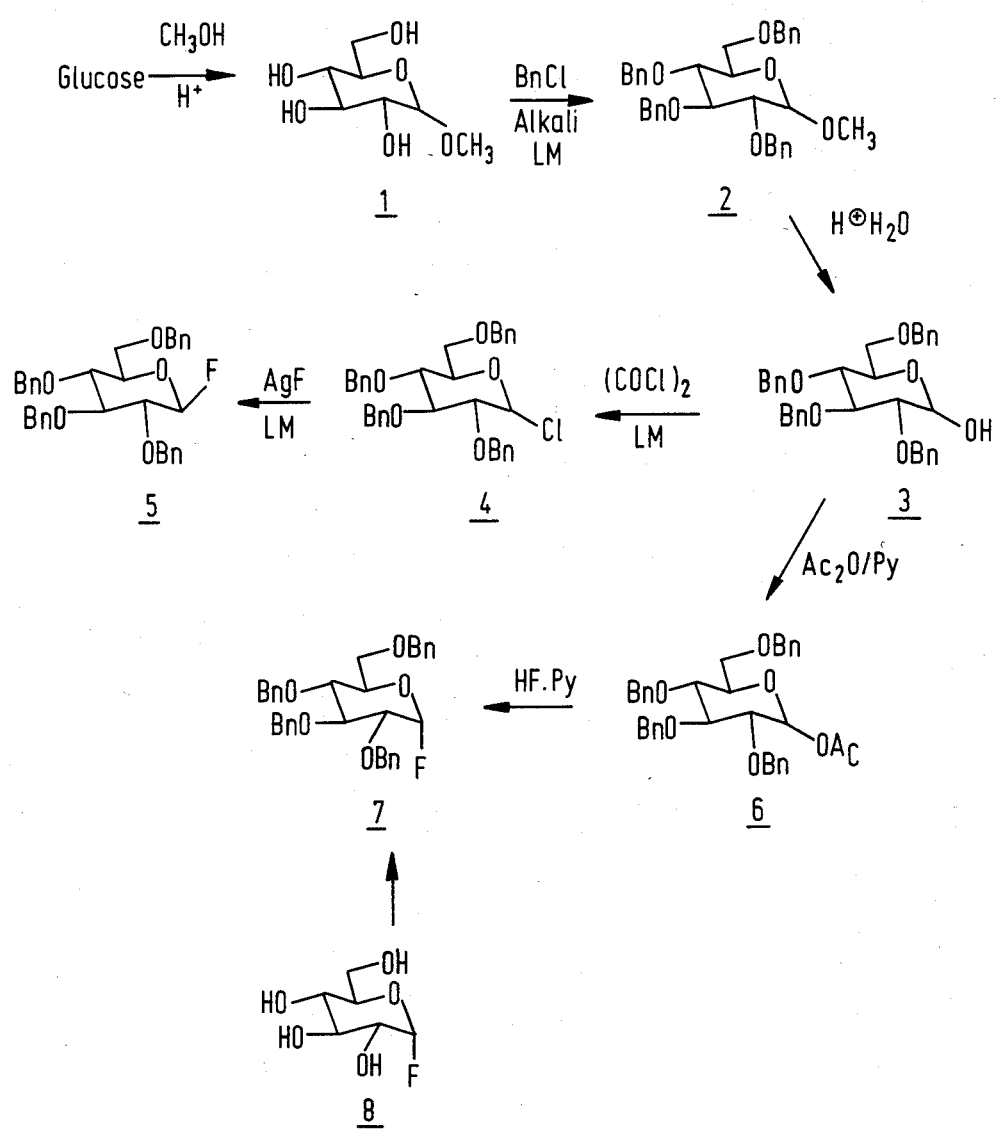

United States Patent [19]

Thiem et al.

[11] Patent Number: 4,803,263

[45] Date of Patent: Feb. 7, 1989

[54] PROCESS FOR THE PREPARATION OF ALKYLATED GLYCOSYL FLUORIDES FREE FROM HYDROXYL GROUPS

[75] Inventors: Joachim Thiem, Münster; Hans-Matthias Deger, Hofheim am Taunus; Wolfram Fritsche-Lang, Bensheim; Matthias Kreuzer, Münster, all of Fed. Rep. of Germany

[73] Assignee: Hoechst Aktiengesellschaft, Frankfurt am Main, Fed. Rep. of Germany

[21] Appl. No.: 894,197

[22] Filed: Aug. 7, 1986

[30] Foreign Application Priority Data

Aug. 9, 1985 [DE] Fed. Rep. of Germany ....... 3528654

[51] Int. Cl.$^4$ ..................... C07H 15/00; C07H 19/00; C07H 21/00
[52] U.S. Cl. ..................................... 536/18.6; 536/22; 536/124
[58] Field of Search .................. 536/124, 22, 18.6

[56] References Cited

U.S. PATENT DOCUMENTS 4,228,274 10/1980 Ponpipom et al. ............... 536/22
4,659,810 4/1987 Thiem et al. ..................... 536/22
4,719,294 1/1988 Rademacher et al. ............ 536/22

OTHER PUBLICATIONS

R. J. Ferrier, "Methds in Carbohydrate Chemistry", vol. 6, 1972, pp. 307–311.
J. E. G. Barnett, Carbohydrate Research, vol. 9, 1969, pp. 21–31.
Chemical Abstracts No. 186733k, vol. 104, No. 21, May 26, 1986.
Windholz et al., "The Merck Index", ONR-96.
Journal of the Chemical Society, Chemical Communications, No. 17, 1984, pp. 1155–1156.
Hayashi et al., Simple Synthesis of Glycosyl Fluorides, pp. 1747–1750.
Klemer et al., Chemische Berichte, 96, 1963, p. 1974.

*Primary Examiner*—Ronald W. Griffin
*Attorney, Agent, or Firm*—Finnegan, Henderson, Farabow, Garrett, & Dunner

[57] ABSTRACT

Alkylated glycosyl fluorides free from hydroxyl groups can be prepared by converting glycosyl fluorides which still contain hydroxyl groups into the alkylated compounds in the manner of Williamson's ether synthesis in the presence of basic systems by means of alkylating agents.

16 Claims, 2 Drawing Sheets

PROCESS FOR THE PREPARATION OF ALKYLATED GLYCOSYL FLUORIDES FREE FROM HYDROXYL GROUPS

Hitherto the glycosyl halides have virtually only been investigated and employed in carbohydrate chemistry in the case of the chlorine and bromine compounds in the form of protected derivatives. Even these, however, display only a restricted stability, which can be demonstrated by their reaction with bases—such as diethylamine—in aprotic solvents to give acylated hydroxyglycals (R. J. FERRIER, Meth. Carbohydr. Chem. 6, 307 (1972)).

Amongst unprotected glycosyl halides, only the glycosyl fluorides, especially the α-glycosyl fluorides, are relatively stable. Kinetic experiments carried out on these have, however, also shown that hydrolytic decomposition takes place not only under base catalysis, but particularly in the case of acid catalysis (J. E. G. BARNETT, Carbohydr. Res. 9, 21 (1969)).

The availability of peralkylated glycosyl fluorides as a glycosylating agent is of particular interest for the synthesis of complex chiral compounds, such as lower oligosaccharides, since meanwhile some new processes for the use thereof in glycosylating reactions have been developed (German Patent Application P 3,426,074.9 (1984)). The only representatives of this class of substances hitherto known are the two anomeric fluorides 5 and 7 (see FIG. 1), multi-stage syntheses thereof from glucose being shown in this Figure. For the preparation of 5, the α-methyl glucoside 1, which is accessible from glucose, is converted, by means of Williamson's ether synthesis, into the tetra-O-benzyl derivative 2, which is converted into the desired 5 via the stages of C-1-hydrolysis, C-1-chlorination and C-1-fluoridation with silver fluoride (C. P. J. GLAUDEMANS and H. G. FLETCHER Jr., Meth. Carbohydr. Chem. 6, 373 (1972); J. R. POUGNY, M. A. N. NASSR, N. NAULET and P. SINAY, Nouv. J. Chem. 2, 389 (1978); T. MUKAIYAMA, Y. MURAI and S. SHODA, Chem. Lett. 1981, 431)). The preparation of the corresponding 7 via the acetylation of 3 to give the α-acetate 6 and subsequent treatment with the pyridine/hydrogen fluoride adduct (Olah's reagent) has been described (S. HASHIMOTO, M. HAYASHI and R. NOYORI, Tetrahedron Lett. 25, 1379 (1984)).

It has now been found, surprisingly, that the unprotected glycosyl fluorides are astonishingly stable to bases in dipolar-aprotic solvents. This opens up the possibility of a novel access to alkylated, in particular peralkylated, glycosyl fluorides free from hydroxyl groups.

The invention therefore relates to a process for the preparation of alkylated glycosyl fluorides free from hydroxyl groups, which comprises converting (by the method of Williamson's ether synthesis) glycosyl fluorides which still contain hydroxyl groups into the "alkylated" compounds by means of "alkylating agents" in the presence of basic systems of oxides and/or hydroxides of the first group of the periodic system, i.e. alkali metal hydroxides, such as sodium hydroxide or potassium hydroxide, or oxides, such as silver oxide, and also alkali metal alcoholates in which the alcohol component has up to 6, in particular up to 4, carbon atoms, such as potassium tert.-butylate, and of alkali metal hydrides, such as sodium hydride (method used by R. E. WING and J. N. BEMILLER Meth. Carbohydr. Chem. 6, 368 (1972)). Here and in the text below, the term "alkylated" means that a saturated aliphatic carbon atom to which, in turn, either hydrogen or further hydrocarbon radicals are attached is introduced into the ether bonds by means of the "alkylating agent". The alkylating agents used are preferably the halogen derivatives, in particular the corresponding chlorine, bromine and iodine compounds, such as methyl iodide. The dialkyl sulfates can, however, also be employed with advantage. In other words, the following are suitable ether radicals: methyl or, in combination with saturated hydrocarbon radicals, ethyl, n-propyl, isopropyl, the various butyls, hexyls, octyls, dodecyls, hexadecyls, octadecyls or $C_{20}$ compounds, such as 2-ethylhexyl, lauryl, palmityl or stearyl; in combination with unsaturated hydrocarbon radicals this should be understood as meaning, for example: allyl, crotyl, diisobuenyl, oleyl and also benzyl, benzhydryl and trityl, and also multinuclear systems, such as —$CH_2$-naphthyl up to a total number of carbon atoms of 25, each of which can also contain, on the aromatic nucleus, radicals having one or more electron-attracting or electron-repelling substituents, such as methoxy, methyl, halogen, nitro or nitrile groups.

The process is preferably carried out in a dipolar-aprotic solvent, such as dimethylformamide, dimethyl sulfoxide, hexamethylphosphoric acid triamide (HMPT) or dimethylpropyleneurea (DMPU). Other bases, such as calcium oxide, potassium carbonate or 1,5-diazabicyclo-[5,4,0]-undec-5-ene (DBU) are not effective.

The process according to the invention thus constitutes a simple, one-stage method for the preparation of glycosyl fluorides, in particular peralkylated glycosyl fluorides, which are suitable for use as starting compounds for the isolation of glycosides (German Patent Application P 3,426,074.9 (1984)).

The starting materials generally used for the process according to the invention are glycosyl fluorides in which all the hydroxyl groups are still unsubstituted. However, it is also possible to use partially acylated glycosyl fluorides, so that mixed acylated and alkylated glycosyl fluorides are obtained. Silver oxide has proved particularly suitable as a base for the reaction of such partially acylated glycosyl fluorides. Acylalkylglycosyl fluorides of this type are suitable for the synthesis of complex branched, lower oligosaccharides.

In addition to α-glucosyl fluoride, suitable starting compounds are also the α-fluorides of other reducing monosaccharides or oligosaccharides—this term embracing 2-4 structural units—such as the α-fluorides of galactose, mannose, gulose, talose, allose, altrose and the like, including the α-fluorides belonging to the series of $C_5$-aldoses, such as xylose, ribose and the like, or, in the case of the oligosaccharides, especially the α-fluorides of the disaccharides, such as lactose, maltose, cellobiose, gentiobiose and the like, or higher saccharides, such as maltotriose, raffinose, maltotetraose and stachyose. The process according to the invention is also applicable to the fluorides of N-acylaminodeoxy-sugars, such as N-acetylaminoglucopyranosyl fluoride.

It is thus possible, by using the process according to the invention, to obtain, inter alia, the crystalline compounds, in part not hitherto described, 2,3,4,6-tetra-O-benzyl-α-D-galactopyranosyl fluoride (10), 2-acetamido-3,4,6-tri-O-benzyl-2-deoxy-α-D-glucopyranosyl fluoride (12), 2,3,6-tri-O-benzyl-4-O(2,3,4,6-tetra-O-benzyl-β-D-galactopyranosyl)-α-D- glucopyranosyl fluoride (14) and 2,3,4,6-tetra-O-methyl-α-D-glucopyranosyl fluoride (15) in an excellent yield.

The reaction according to the invention is advantageously carried out between −20° C. and +40° C., preferably between −5° C. and +25° C., and in general under atmospheric pressure. The use of excess or reduced pressure is possible, but not preferable.

Figure 2:
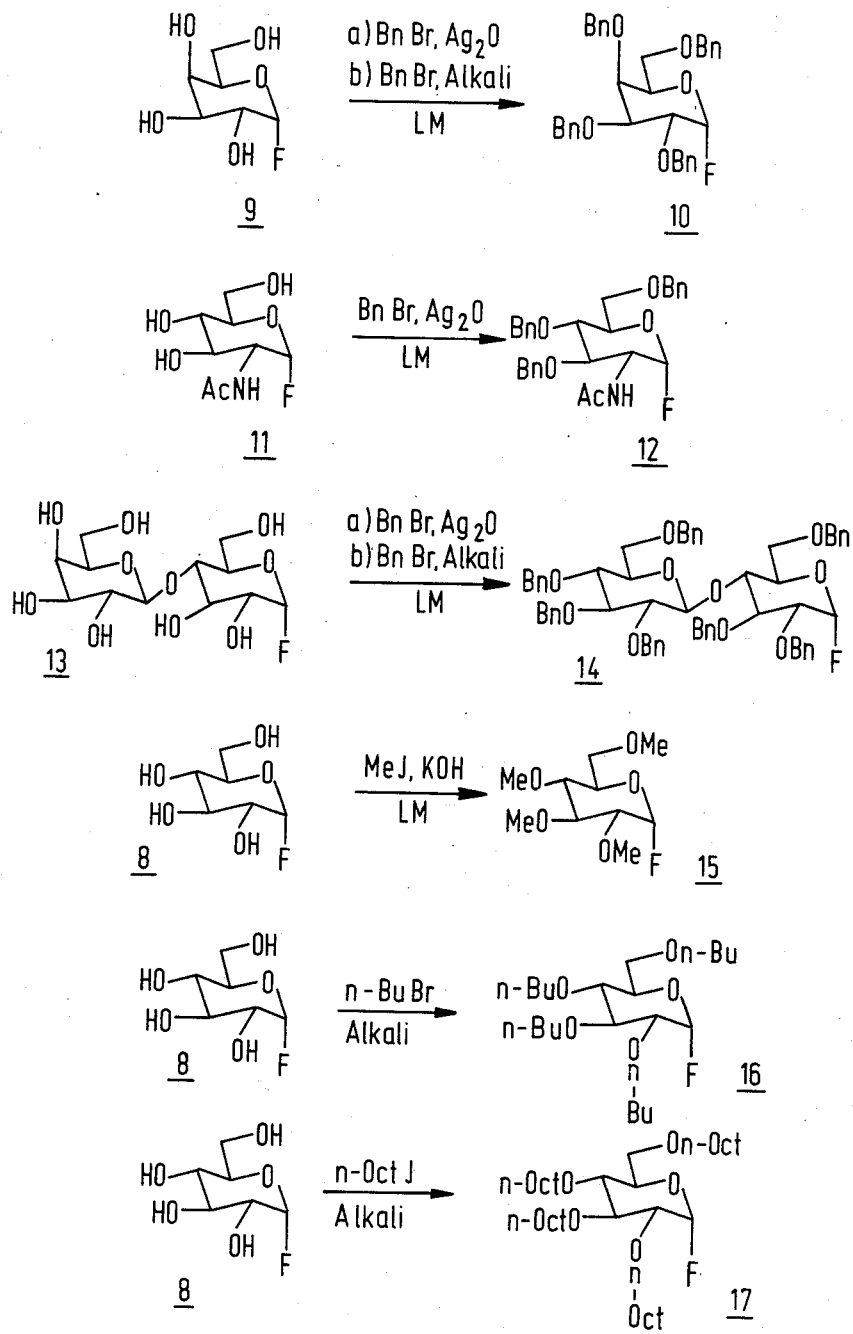

In the examples which follow, the solvent data relate in each case to volume. In FIGS. 1 and 2, Bn denotes benzyl, S denotes solvent, Py pyridine, Me denotes methyl n-BuBr denotes 1-bromobutane and n-Oct-I denotes 1-iodoctane.

EXAMPLES 1. 2,3,4,6-tetra-O-benzyl-2-D-glucopyranosyl fluorides (7):

(a) 2.6 g (14.3 mmol) of 8 were dissolved in 50 ml of anhydrous dimethylformamide and stirred, at room temperature, with 26.5 g (114 mmol) of freshly prepared silver oxide and 14 ml (20 g, 118 mmol) of benzyl bromide. The reaction was complete after one hour, as can be established by thin layer chromatography in 20:1 methylene chloride/diethylether (ether). The solution was filtered through a silicate filter aid (®Celite) and the filtrate was concentrated under high vacuum. It was possible to purify the crude product by crystallization from ether or by column chromatography (5:1 n-hexane/ether). Yield 6.5 g (85%).

(b) 2.0 g (11 mmol) of 8 were dissolved in 20 ml of absolute dimethylformamide, and 7.4 g (132 mmol) of powdered potassium hydroxide and 15 ml of benzyl bromide were added at 0° C. The mixture was allowed to warm up to room temperature and was stirred for a further 3 hours. The reaction mixture was then stirred for 30 minutes with 15 ml of methanol, then poured into iced water and extracted with twice 50 ml of methylene dichloride, and the extract was dried over magnesium sulfate, filtered and concentrated under high vacuum. The residue crystallized excellently from n-hexane/ether; yield 5.2 g (87%).

Melting point 70.5° C., $[\alpha]_D^{20}=4.2$ (c=0.87 in CHCl$_3$).

$^1$H-NMR (CDCl$_3$): $\delta=5.55$ (dd, 1-H), $J_{1,2}=2.5$, $J_{1,F}=52.9$ Hz.

2. 2,3,4,6-tetra-O-benzyl-α-D-galactopyranosyl fluoride (10):

(a) 2.6 g (14.3 mmol) of 9 were reacted and worked up under same conditions as in Example 1a. The new compound 10 is obtained in a yield of 5.7 g (74%).

(b) 1.82 g (10.0 mmol) of 9 were reacted and worked up as in Example 1b; yield 4.0 g (75%).

Melting point 71° C.; Syrup, $[\alpha]_D^{20}=+3.9$ (c=1.14 in CHCl$_3$). $^1$H-NMR (C$_6$D$_6$): $\delta=5.68$ (dd, 1-H), $J_{1,2}=2.7$, $J_{1,F}=53.9$ Hz.

3. 2-acetamido-3,4,6-tri-O-benzyl-2-deoxy-α-D-glycopyranosyl fluoride (12):

A solution of 2.85 g (14.3 mmol) of 11 was reacted and worked up as in Example 1a. Yield 5.9 g (77%), melting point 188° C., $[\alpha]_D^{20}=+81.8$ (c=0.92 in CHCl$_3$).

$^1$H-NMR (CDCl$_3$): $\delta=5.61$ (dd, 1-H), $J_{1,2}=2.4$, $J_{1,F}=53.0$ Hz.

4. 2,3,6-tri-O-benzyl-4-O(2,3,4,6-tetra-O-benzyl-β-D-galactopyranosyl)-α-D-glucopyranosyl fluoride (14):

(a) 10.0 g (43 mmol) of silver oxide and 5 ml (43 mmol) of benzyl bromide were added at 0° C. to a solution of 1.07 g (3.1 mmol) of 13 in 30 ml of absolute dimethylformamide. The mixture was allowed to warm up to room temperature and stirred for a further 2 hours. It was then filtered through silica gel, and the filtrate was concentrated under high vacuum. The residue was purified over a short silica gel column using 3:1 n-hexane/ether. Yield 2.2 g (72%).

(b) 1.72 g (5.0 mmol) of 13 are reacted and worked up as in Example 1b; yield 3.46 g (71%).

Melting point 81° C., $[\alpha]_D^{20}=-0.3$, (c=6.33 in CHCl$_3$).

$^1$H-NMR (CDCl$_3$): $\delta=5.49$ (dd, 1-H), $J_{1,2}=2.6$, $J_{1,F}=53.0$ Hz, 4.70 (d, 1'-H), $J_{1',2'}=7.6$ Hz.

5. 2,3,4,6-tetra-O-methyl-α-D-glucopyranosyl fluoride (15):

500 mg (2.75 mmol) of 8 were dissolved in 10 ml of anhydrous dimethylformamide, and 1.25 g (22.3 mmol) of powdered potassium hydroxide and 1.4 ml (22.3 mmol) of methyl iodide were added at room temperature. After 1 hour at room temperature, the mixture is cooled to 0° C., 5 ml of methanol are added and the mixture is stirred for 30 minutes. The mixture is then poured into ice water and extracted with 50 ml of methylene dichloride twice, and the extract is dried over magnesium sulfate and concentrated. The pure compound is isolated by purification by chromatography over silica gel using 2:1 toluene/ethyl acetate; yield 523 mg (80%), viscose liquid, $[\alpha]_D^{20}=+97.3$ (c=2.72 in CHCl$_3$). $^1$H-NMR (CDCl$_3$): $\delta=5.37$ (dd, 1-H), $J_{1,2}=2.7$, $J_{1,F}=53.1$ Hz.

6. 2,3,4,6-tetra-O-n-butyl-α-D-glucopyranosyl fluoride (16):

0.5 g (2.7 mmol) of α-D-glucopyranosyl fluoride (8) are dissolved in 10 ml of anhydrous dimethylformamide, and 1.8 g (33 mmol) of powdered potassium hydroxide and 4.5 g (3 ml, 33 mmol) of 1-bromobutane are added. After 3 hours at 70° C. (water bath), 10 ml of methanol are added and the mixture is stirred for a further 30 minutes. After cooling, the solution is poured into ice water, the aqueous phase is extracted three times with methylene chloride and the extracts are dried over magnesium sulfate. Concentration under high vacuum gives 0.8 g of a brown syrup, which is purified by chromatography (20:1 toluene/ethyl acetate). Yield 520 mg (42%), colorless syrup, $[\alpha]_D^{20}=+61.7$ (c=0.92, CHCl$_3$), $^1$H-NMR (C$_6$D$_6$): $\delta=5.61$ (dd, 1-H), $J_{1,2}=2.6$, $J_{1,F}=53.9$ Hz.

7. 2,3,4,6-tetra-O-n-octyl-α-D-glucopyranosyl fluoride (17):

260 mg (1.4 mmol) of α-D-glucopyranosyl fluoride (8) are dissolved in 10 ml of anhydrous dimethylformamide and heated at 70° C. together with 0.95 g (17 mmol) of powdered potassium hydroxide and 3.1 ml (4.1 g, 17 mmol) of 1-iodoctane. After 6 hours, 5 ml of methanol are added and the mixture is stirred for a further 30 minutes without heating. After cooling, the reaction mixture is poured into ice water and the aqueous phase is extracted three times with methylene chloride. The extracts are dried over magnesium sulfate and concentrated to give 490 mg of a crude product, which is purified by chromatography (20:1 toluene/ethyl acetate). Yield 305 mg (34%), colorless syrup, $[\alpha]_D^{20}=+32.8$ (C=1.27, CHCl$_3$), $^1$H-NMR (C$_6$D$_6$): $\delta=5.66$ (dd, 1-H), $J_{1,2}=2.6$, $J_{1,F}=53.6$ Hz.

What we claim is:

1. A process for the preparation of alkylated glycosyl fluorides free from hydroxyl groups, which comprises alkylating glycosyl fluorides which contain hydroxyl groups with alkylating agents capable of producing an ether linkage between a saturated aliphatic hydrocarbon atom and oxygen, in the presence of a basic system of at least one compound selected from the group consisting of an oxide of the first group of the periodic table, a hydroxide of the first group of the periodic table, an alkali metal alcoholate in which the alcohol component has up to 6 carbon atoms, and an alkali metal hydride.

2. The process as claimed in claim 1, wherein the alkylating agent contains at least one aromatic radical on the saturated carbon atom.

3. The process as claimed in claim 1, wherein the alkylating agent is a chlorine, bromine, or iodine compound of an aliphatic hydrocarbon radical.

4. The process as claimed in claim 1, wherein the reaction is carried out in the presence of silver oxide or an alkali metal hydroxide.

5. The process as claimed in claim 1, wherein the reaction is carried out in a dipolar-aprotic solvent.

6. The process as claimed in claim 1, wherein the reaction is carried out at $-20°$ to $+40°$ C.

7. The process as claimed in claim 1, wherein all the OH groups in the glycosyl fluoride used as the starting material are unsubstituted.

8. The process as claimed in claim 1, wherein the glycosyl fluoride used as the starting material has been partially acylated.

9. The process as claimed in claim 2, wherein the alkylating agent is a benzyl compound.

10. The process as claimed in claim 3, wherein the aliphatic hydrocarbon radical contains at most one olefinic bond.

11. The process as claimed in claim 4, wherein the alkali metal hydroxide is potassium hydroxide.

12. The process as claimed in claim 5, wherein the dipolar-aprotic solvent is dimethylformamide.

13. The process as claimed in claim 6, wherein the reaction is carried out at $-5°$ to $+25°$ C.

14. 2-acetamido-3,4,6-tri-O-benzyl-2-deoxy-α-D-glucopyranosyl fluoride.

15. 2,3,4,6-tetra-O-n-butyl-α-D-glucopyranosyl fluoride.

16. 2,3,4,6-tetra-O-n-octyl-α-D-glucopyranosyl fluoride.

* * * * *